(12) United States Patent
Kidooka (10) Patent No.: US 6,964,662 B2
(45) Date of Patent: Nov. 15, 2005

(54) ENDOSCOPIC FORCEPS INSTRUMENT (75) Inventor: Satoshi Kidooka, Tokyo (JP)

(73) Assignee: PENTAX Corporation, Tokyo (JP)

( * ) Notice: Subject to any disclaimer, the term of this patent is extended or adjusted under 35 U.S.C. 154(b) by 142 days.

(21) Appl. No.: 10/404,559

(22) Filed: Apr. 2, 2003

(65) Prior Publication Data
US 2003/0191464 A1    Oct. 9, 2003

(30) Foreign Application Priority Data

Apr. 9, 2002   (JP) ............................. 2002-106012
Sep. 25, 2002  (JP) ............................. 2002-278651

(51) Int. Cl.⁷ ........................ A61B 18/12; A61B 17/28
(52) U.S. Cl. ........................ 606/52; 606/205; 606/207
(58) Field of Search ................... 600/101; 606/41–52

(56) References Cited

U.S. PATENT DOCUMENTS

| 5,035,248 A | * | 7/1991 | Zinnecker ................. 600/564 |
| 5,330,471 A | * | 7/1994 | Eggers ..................... 606/48 |
| 5,762,613 A | * | 6/1998 | Sutton et al. .............. 600/564 |
| 5,843,000 A | * | 12/1998 | Nishioka et al. ........... 600/566 |
| 5,906,630 A | * | 5/1999 | Anderhub et al. .......... 606/205 |
| 6,063,103 A | * | 5/2000 | Hashiguchi ............... 606/205 |
| 6,066,102 A | * | 5/2000 | Townsend et al. .......... 600/564 |
| 6,083,240 A |   | 7/2000 | Ouchi |
| 6,129,683 A | * | 10/2000 | Sutton et al. ............. 600/564 |
| 6,887,240 B1 | * | 5/2005 | Lands et al. .............. 606/51 |
| 2001/0021859 A1 | * | 9/2001 | Kawai et al. ............. 606/205 |
| 2002/0123667 A1 |   | 9/2002 | Ouchi |

FOREIGN PATENT DOCUMENTS

| JP | 61263443 | 11/1986 |
| JP | 8-140987 | 6/1996 |
| JP | 2002-253570 | 9/2002 |

* cited by examiner

Primary Examiner—Henry M Johnson, III
(74) Attorney, Agent, or Firm—Greenblum & Bernstein, P.L.C.

(57) ABSTRACT

An endoscopic forceps instrument has an inserting portion to be inserted into a body cavity through an endoscope, a clevis, a pair of rivets, and a pair of opposing jaws. The clevis is coupled to a distal end of the inserting portion. The pair of rivets is coupled to the clevis. Each of the rivets has a tip end that is swaged in order to fix the rivet to the clevis. The pair of opposing jaws is pivotably coupled to respective rivets so as to be movable between an open position and a closed position. The pair of rivets is arranged in parallel to each other. Further, the pair of rivets is arranged such that the tip ends thereof, which are swaged and therefore having relatively low mechanical strength, are located and swaged at opposite sides of the clevis.

12 Claims, 9 Drawing Sheets

ENDOSCOPIC FORCEPS INSTRUMENT

BACKGROUND OF THE INVENTION

The present invention relates to an endoscopic forceps instrument having a pair of opposed jaws at the distal end thereof.

Typical endoscopic forceps instruments having a pair of opposed jaws include, for example, biopsy forceps, grasping forceps, and hemostatic forceps.

Figure 1:
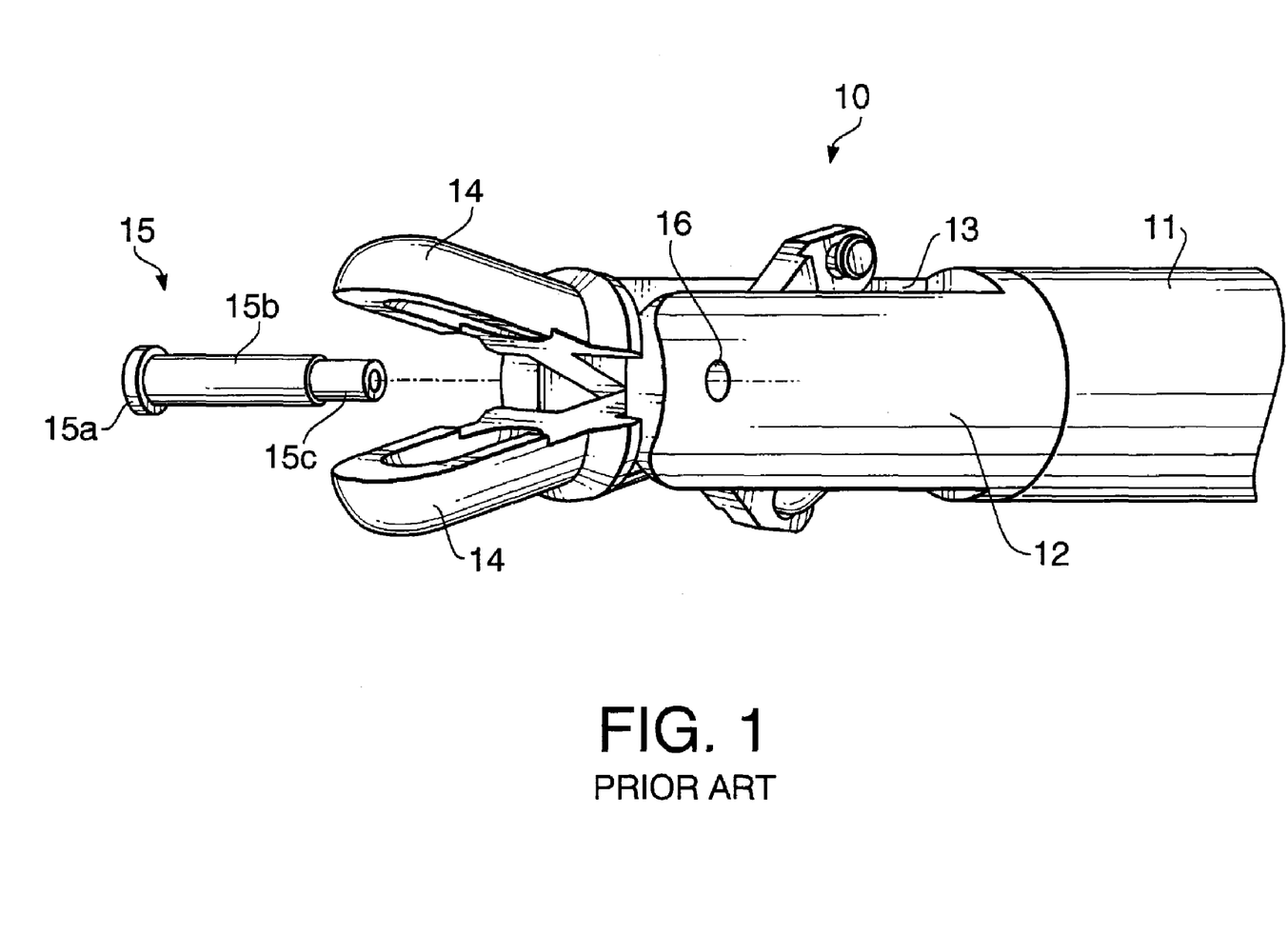
FIG. 1 shows a distal end of a conventional endoscopic forceps instrument.

FIG. 1 shows a distal end of a conventional endoscopic forceps instrument 10. The endoscopic forceps instrument 10 includes a clevis 12 coupled to the distal end of a flexible sheath 11. A pair of opposing jaws 14 is pivotably coupled to the distal end of the clevis 12 by a rivet 15. The rivet 15 is inserted into the bores 16 formed to the distal end of the clevis, and extends across the slit 13 of the clevis 12.

A pair of control wires (not shown) are inserted through the sheath 11 and connected to the pair of jaws 14. The pair of opposed jaws 14 open and close if the pair of wires is operated back and forth along the sheath 11 from the proximal end of the endoscopic forceps instrument 10.

The rivet 15 includes a body 15b, a head 15a having larger diameter than a body 15b, and a tip portion 15c having smaller diameter than the body 15b. The tip portion 15c is swaged after the rivet 15 is inserted into the bores 16 of the clevis 12 to fix the rivet 15 to the clevis 12. However, since the mechanical strength of the swaged tip portion 15c of the rivet 15 is relatively low, the rivet 15 comes off from the clevis 15, and hence the distal end of the forceps instrument becomes disassembled, when a large force is exerted on the clevis 15 that acts to widen the slit 13 of the clevis.

Thus, there is a need for an endoscopic forceps instrument of which the distal end does not readily come apart upon application of a large force.

SUMMARY OF THE INVENTION

The invention is advantageous in that an instrument that satisfies the above-mentioned need is provided.

According to an aspect of the invention, there is provided an endoscopic forceps instrument having an inserting portion to be inserted into a body cavity through an endoscope. The endoscopic forceps instrument includes a clevis, a pair of rivet members, and a pair of opposing jaws.

The clevis is coupled to a distal end of the inserting portion. The pair of rivet members are inserted through bores formed to the clevis and thereby coupled to the clevis. Each of the rivet members has a head formed at one end thereof and an engaging portion formed at other end thereof. The head is formed in a shape and size that does not allow the head to pass through the bores. The engaging portion is engaged with the clevis, e.g., being swaged or screw coupled, to fix the rivet member to the clevis. The pair of opposing jaws is pivotably coupled to respective rivet members so as to be movable between an open position and a closed position. The pair of rivet members is arranged in parallel to each other. Further, the pair of rivet members is arranged such that the engaging portions thereof, which may be swaged or screw coupled, for example, and therefore have relatively low mechanical strength, are located at opposite sides of the clevis. In other words, heads of the rivet members, which have larger mechanical strength than the engaged portions, are located at opposite sides of the clevis. Thus, firm engagement between the rivets and the clevis are ensured at both sides of the clevis.

Optionally, the pair of rivet members is arranged such that a longitudinal axis of the clevis passes through a space defined between the pair of rivets.

Optionally, the pair of jaws are made of a conductive material and connected to a pair of wires so that high frequency electric power can be supplied to the pair of jaws. In this case, the endoscopic forceps instrument may further include an insulating block that is supported by the pair of rivets between the pair of jaws to ensure insulation between the jaws.

According to another aspect of the invention, a forceps jaw assembly is provided that includes a clevis having a base to be coupled to a distal end of an inserting portion of an endoscopic forceps instrument, a pair of rivet (or pin or rod) members inserted through bores formed to the clevis to be coupled to the clevis, and a pair of opposing jaws pivotably coupled to respective rivet (or pin or rod) members so as to be movable between an open position and a closed position. Each of the rivet members has a head formed at one end thereof and an engaging portion formed at other end thereof. The head is formed in a shape and size that does not allow the head to pass through the bores. The engaging portion is engaged with the clevis to fix the rivet member to the clevis. The rivet members are arranged in parallel to each other and such that the heads thereof are located at opposite sides of the clevis.

DETAILED DESCRIPTION OF THE EMBODIMENTS

Hereinafter, an embodiment of the invention will be described with reference to the accompanying drawings.

Figure 2:
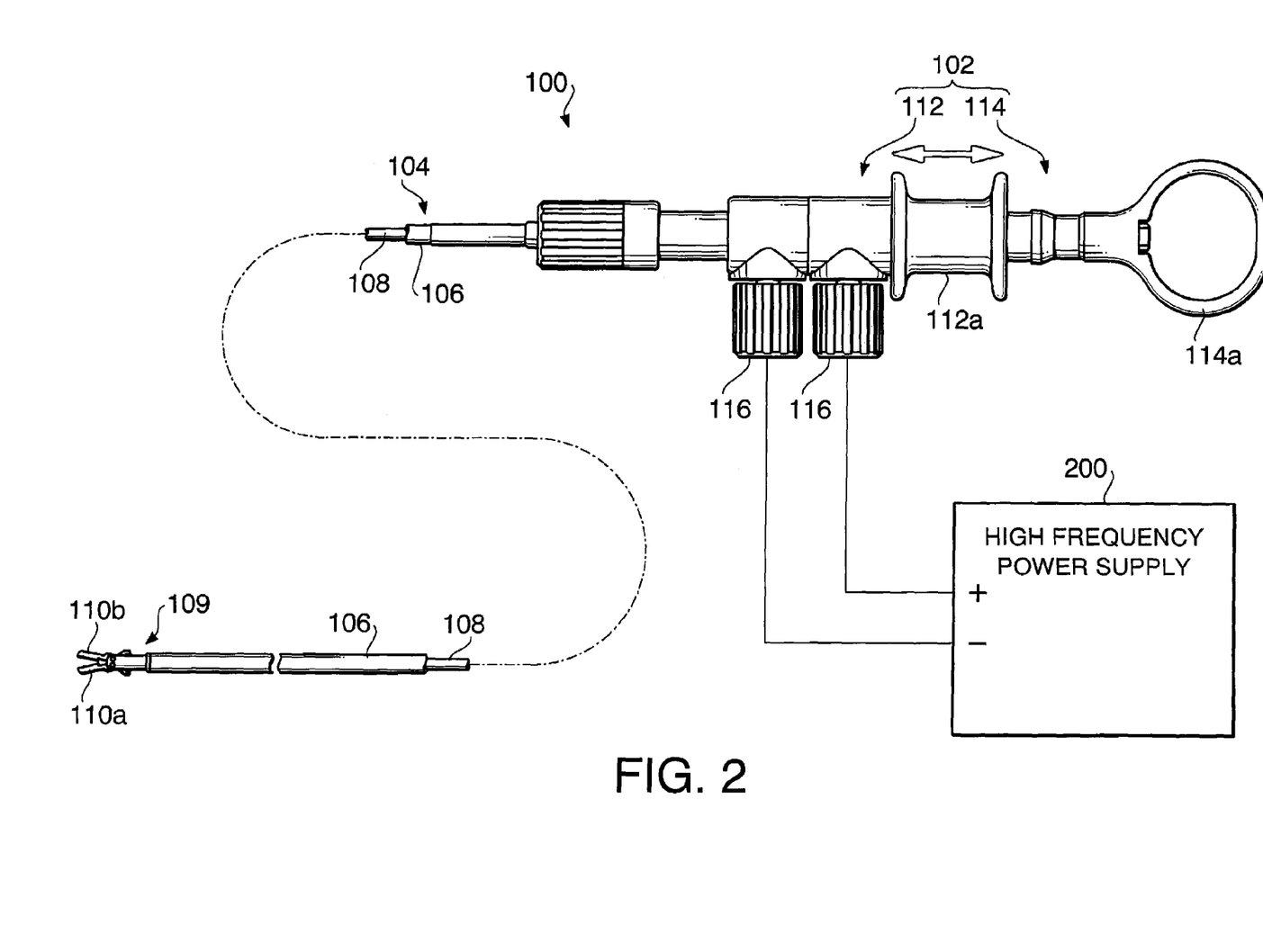
FIG. 2 schematically shows an endoscopic forceps instrument according to an embodiment of the invention connected to a high frequency power supply.

FIG. 2 schematically shows an endoscopic forceps instrument 100 according to an embodiment of the invention connected to a high frequency power supply 200.

The forceps instrument 100 includes an operation portion 102 and an inserting portion 104 connected to the distal end of the operation portion 102.

The inserting portion 104 is provided in a form and size that allows it to be introduced into a body cavity through a treatment tool inserting channel of an endoscope (not shown). The inserting portion 104 includes an elongated, flexible sheath 106, and a pair of conductive wires 108 (only one is shown) slidably passed through the sheath 106. The sheath 106 is made of insulating material such as poly-tetra-fluoro-ethylene (PTFE). In an exemplary embodiment, the sheath 106 is 1 m to 2 m long and has an outer diameter of 2 mm to 3 mm.

A forceps jaw assembly 109 is mounted to the distal end of the inserting portion 104. The forceps jaw assembly 109 includes first and second jaws 110a and 110b that are connected to the conductive wires 108.

The operation portion 102 includes a cylindrical portion 112 and a rod portion 114 slidably inserted into the cylindrical portion 112.

The cylindrical portion 112 has a circumferential groove 112a at a proximal end thereof. A user of the forceps instrument 100 can hold the operation portion 112 by pinching it at the groove 112a with his index finger and long finger.

The rod portion 114 has a ring 114a into which the user can insert his thumb to slide the rod portion 114 within the cylindrical portion 112 back and forth.

The rod portion 114 is connected with the pair of wires 108 in the cylindrical portion 112 such that the wires 108 retract and proceed in the sheath 106 as the rod portion 114 is moved back and forth with respect to the cylindrical portion 112. It should be noted that the pair of wires 108 may be fixed to each other so that they slide integrally within the sheath 106 to move the pair of jaws 110 simultaneously.

The conductive wires 108 are detachably connected to power supply lines of the high frequency power supply 200 via a pair of connectors 116 provided to the side surface of the cylindrical portion 112. One of the conductive wires 106 is connected to the positive terminal of the power supply 200 and the other to the negative terminal.

Figure 3:
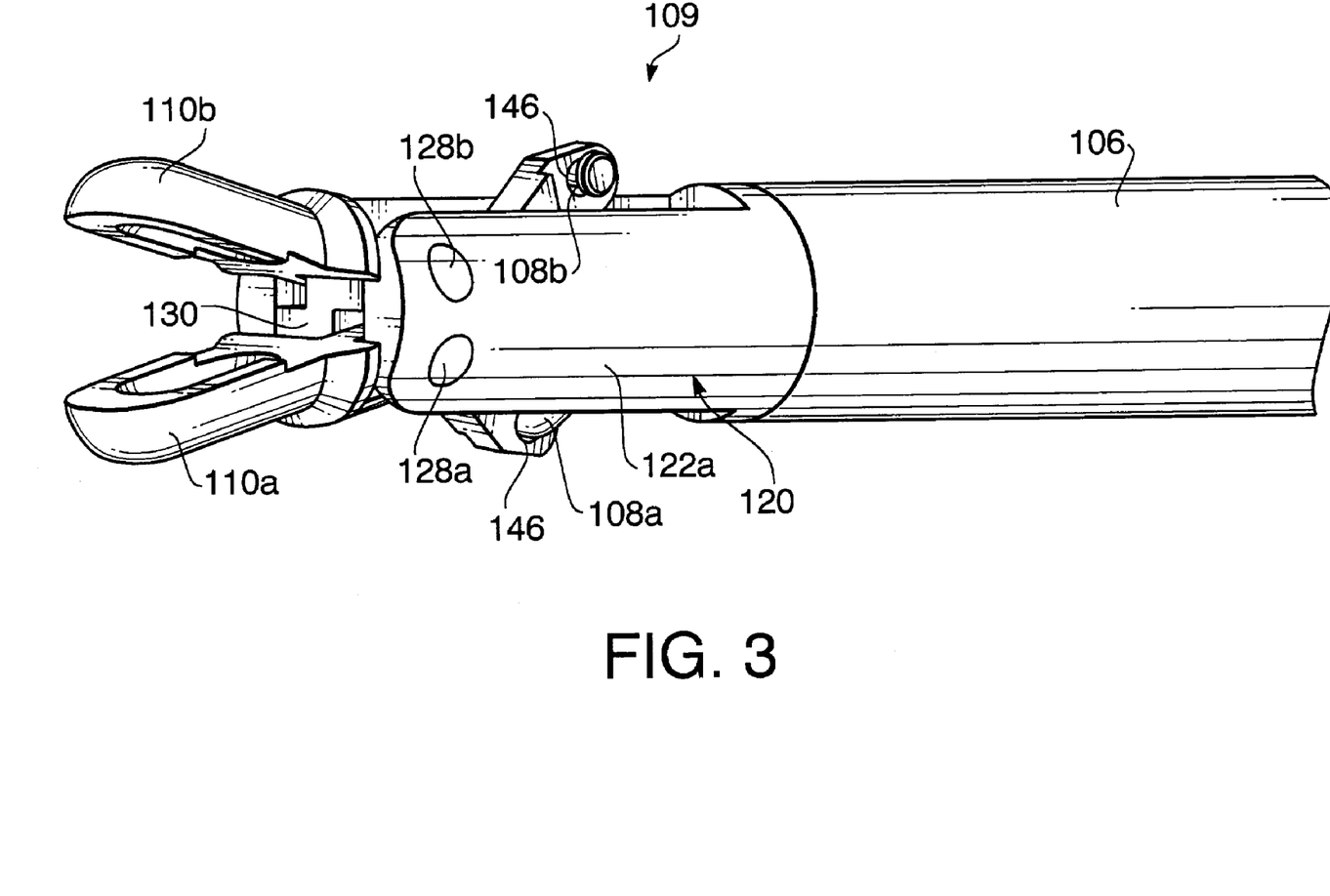
FIG. 3 is a perspective view of the distal end of the endoscopic forceps instrument shown in FIG. 2.
Figure 4:
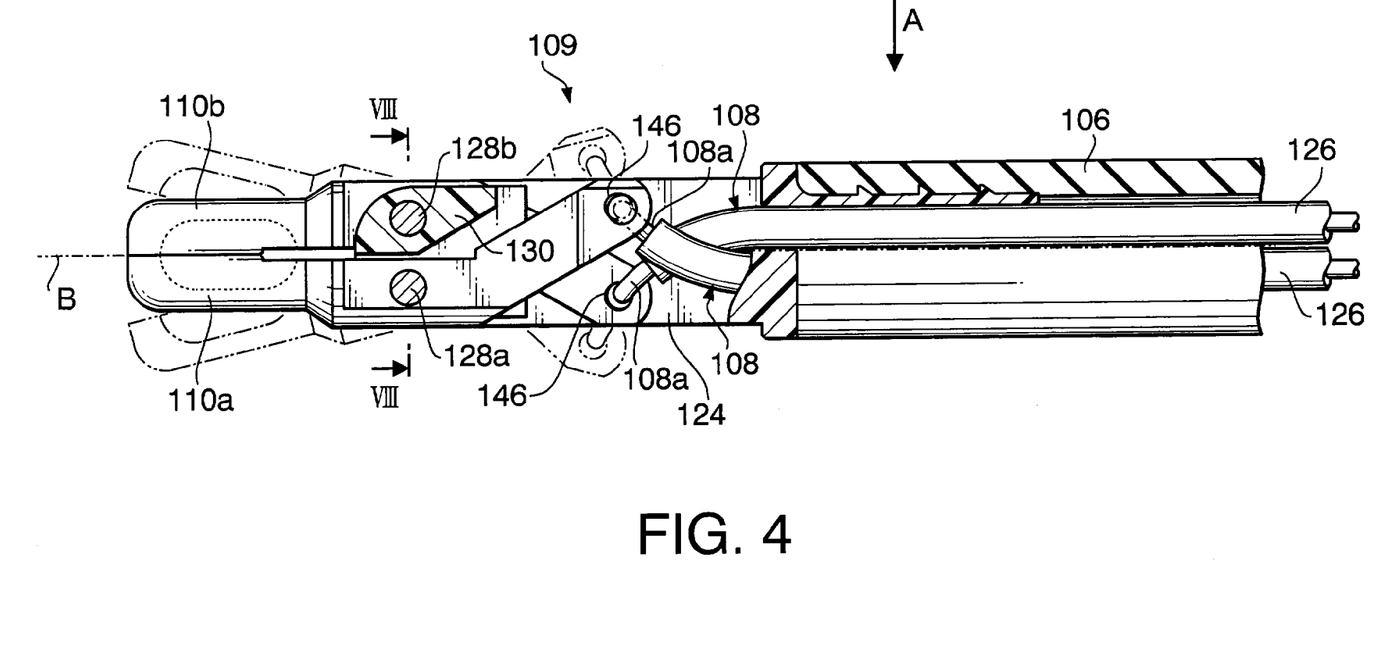
FIG. 4 is a partially sectional side view of the distal end of the endoscopic forceps instrument shown in FIG. 2.
Figure 5:
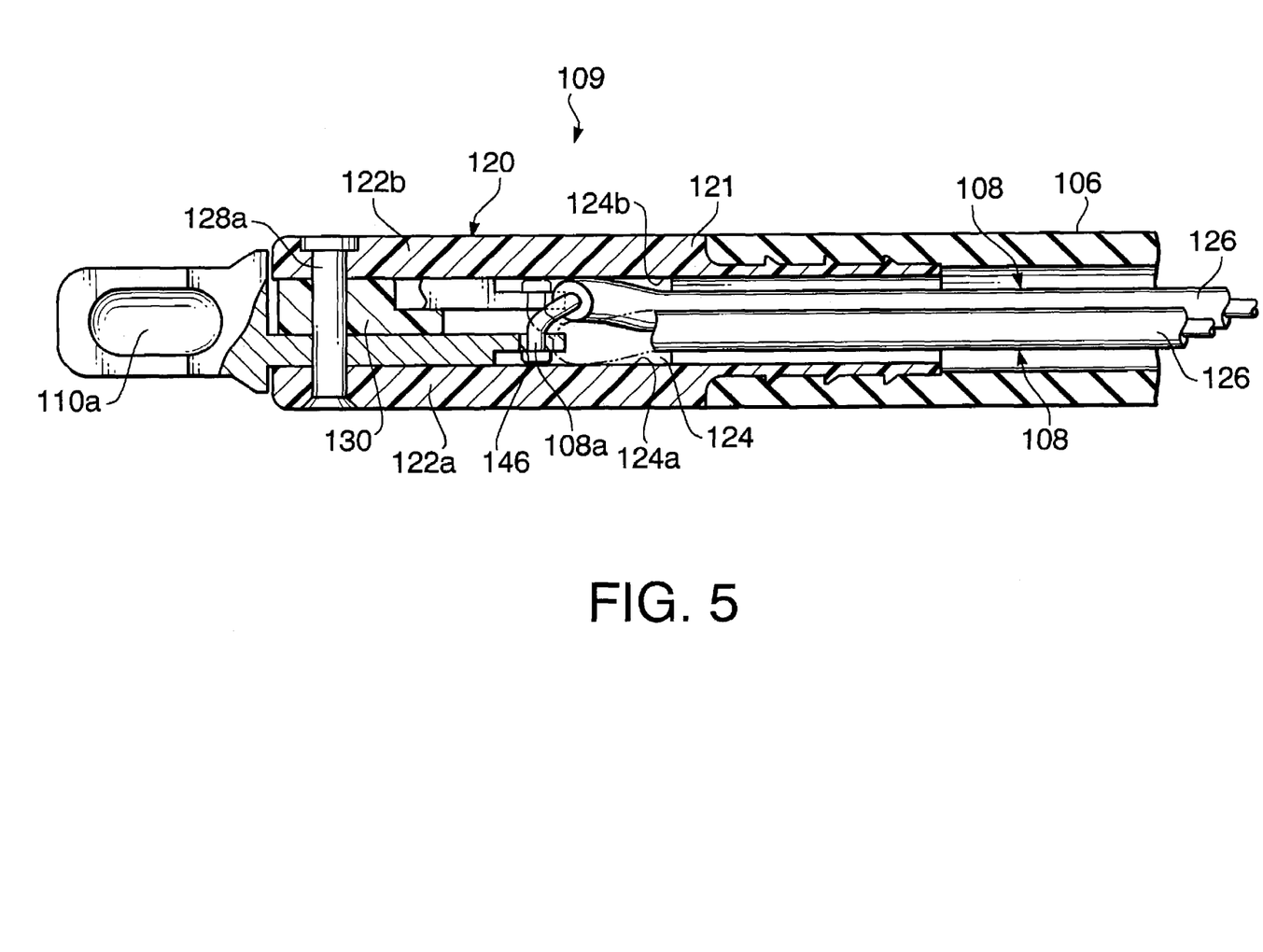
FIG. 5 is a sectional view of the endoscopic forceps instrument shown in FIG. 4 observed from the direction indicated by an arrow A.

FIG. 3 is a perspective view of the distal end of the forceps instrument 100 shown in FIG. 2. FIG. 4 is a partially sectional side view of the distal end of the forceps instrument 100 shown in FIG. 2, and FIG. 5 is a sectional view of the distal end of the forceps instrument 100 shown in FIG. 4 observed from the direction indicated by the arrow A. Note that FIGS. 4 and 5 are drawn as a composite view combining cross sectional views at various positions.

The forceps jaw assembly 109 includes a clevis 120 to which the first and second jaws 110a and 110b are pivotably coupled. The clevis 120 is made of hard insulating material such as rigid plastic and is mounted to the distal end of the flexible sheath 106.

As shown in FIG. 5, the clevis 120 has a base 121 connected to the distal end of the flexible sheath 106 and first and second arms 122a and 122b extending forwards from the base 121 in parallel to each other to form a slit 124 therebetween having a constant width. First and second rivets 128a and 128b are supported by the arms (122a, 122b) in the vicinity of the distal end of the arms (122a and 122b) (see also FIG. 4).

The first and second rivets 128a and 128b are arranged parallel to and spaced apart from each other, and perpendicular to first and second inner side surfaces 124a and 124b of the slit 124. Further, the first and second rivets 128a and 128b are arranged such that the longitudinal axis B of the clevis 120 passes the center of the space defined therebetween. The first and second rivets 128a and 128b are made of stainless steel, for example.

The first and second jaws 110a and 110b are partially inserted into the slit 124 of the clevis 120 and pivotably mounted to the first and second rivets 128a and 128b. Thus, the jaws 110a and 110b can move between a closed position, at which the jaws 110a and 110b come into contact with each other as shown in solid lines in FIG. 4, and an open position, at which the jaws 110a and 110b are located apart from each other as shown in chain double-dashed lies in FIG. 4.

As shown in FIG. 4, the rear ends or proximal ends of the jaws 110a and 110b are connected with the respective conductive wires 108. Each of the conductive wires 108 is covered with a insulating tube 126 except the end portion 108a thereof at which the conductive wire 108 is connected to the corresponding jaw (110a, 110b).

An insulating block 130 is provided in the slit 124 of the clevis 120 to prevent the first and second jaws 110a and 110b from coming into contact to each other within the slit 124. The insulating block 130 is located between the first and second jaws 110a and 110b and supported, by the first and second rivets 128a and 128b.

Figure 6:
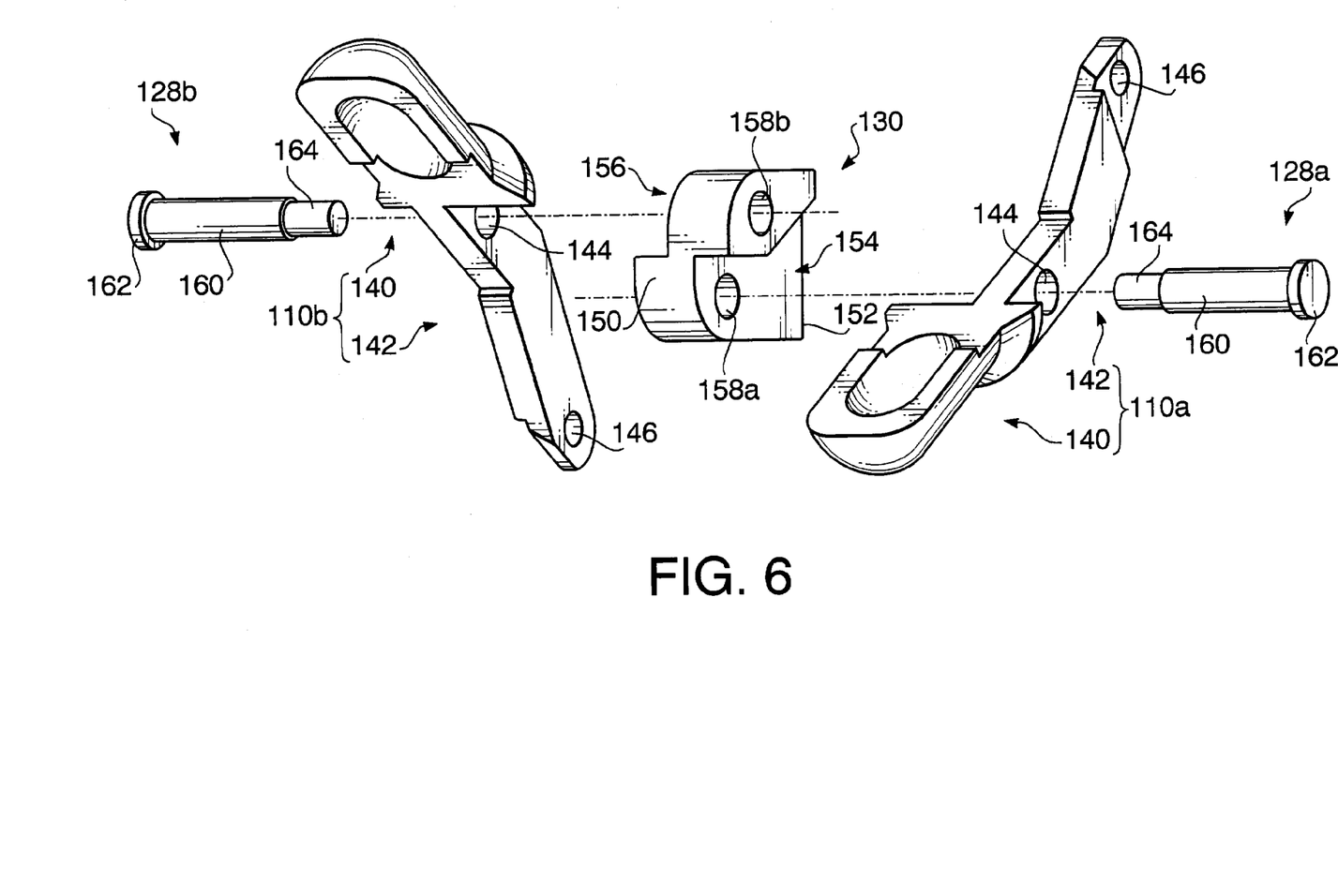
FIG. 6 is an exploded perspective view of a forceps jaw assembly of the endoscopic forceps instrument shown in FIG. 2.

FIG. 6 is an exploded perspective view of the forceps jaw assembly 109. Note that the clevis 120 is not shown in FIG. 6 for clarity of the drawing.

Each of the first and second jaws 110a and 110b is an elongated member made of conductive metal such as stainless steel. Each jaw (110a, 110b) includes an elongated front (distal) portion 140 and an elongated rear (proximal) portion 142. When the jaws 110a and 110b are mounted to the clevis 120, the front portions 140 thereof are located outside of the slit 124 and the rear portions 142 thereof are located between the two arms 122.

Two through holes are formed to the rear portion 142 of each jaw (110a, 110b). The first one is a supporting hole 144 provided at substantially the center of each jaw (110a, 110b). The other one is a connection hole 146 formed in the vicinity of the rear end of each jaw (110a, 110b).

The first jaw 110a is pivotably mounted to the clevis 120 by inserting the first rivet 128a through the supporting hole 144 thereof, while the second jaw 110b is pivotably mounted to the clevis 120 by inserting the second rivet 128b through the supporting hole 144 thereof.

The tip end of each conductive wire 108, which is exposed from the insulating tube 126, is passed through the connecting hole 146 and thereby connected with the corresponding jaw (110a, 110b).

The rear portion 142 of each jaw (110a, 110b) is slightly bent so that the conductive wires 108 sliding back and forth within the sheath 106 can swing the jaws 110a and 110b around the respective rivets 128a and 128b between the open and closed positions.

The front portion 140 of each jaw (110a, 110b) has a cup like shape. The jaws 110a and 110b are arranged such that the cup like portions come in contact with each other at the concave sides thereof when the jaws 110a and 110b are in the closed position.

The insulating block 130 is made of ceramic or resin such as poly-tetra-fluoro-ethylene. The insulating block 130 has front and rear sides (150, 152) and right and left sides (154, 156). The insulating block 130 is located within the slit 124 of the clevis 120 such that the right and left sides (154, 156) face the right and left inner side surfaces 124a and 124b of the slit 124, respectively.

First and second through holes 158a and 158b are formed to the insulating block 130 which are perpendicular to the right and left sides 154 and 156 of the insulating block 130. The insulating block 130 is mounted to the clevis 120 by inserting the first and second rivets 128a and 128b through the first and second through holes 158a and 158b, respectively. Since the insulating block 130 is supported by two rivets (128a, 128b), it does not rotate within the slit 124.

Each of the rivets (128a and 128b) has a body 160, a head 162 having a larger diameter than the body 160, and a tip portion 164 having a smaller diameter than the body 160.

Figure 7A:
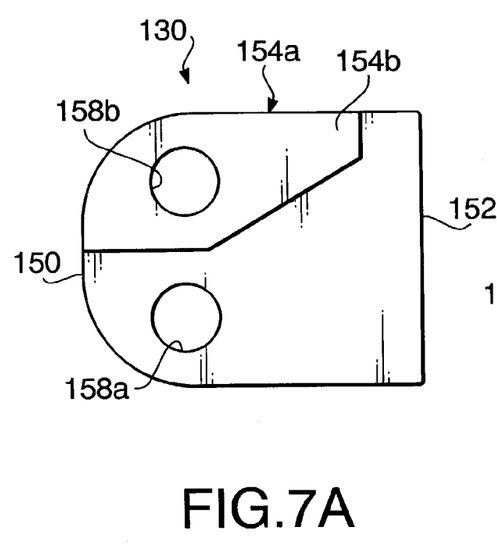
FIGS. 7A and 7B respectively show a right side view and a rear side view of an insulating block of the endoscopic forceps instrument shown in FIG. 2.
Figure 7B:
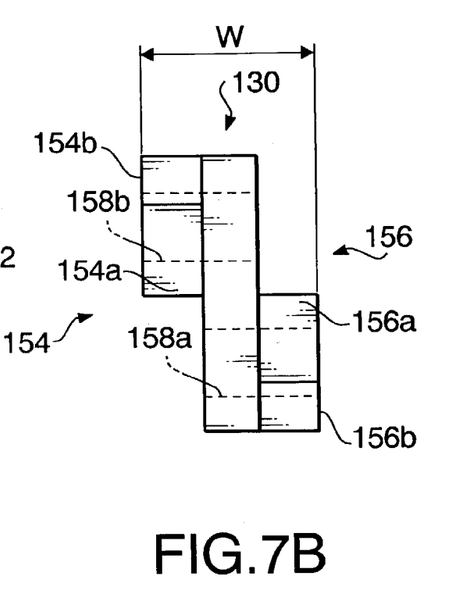

FIGS. 7A and 7B show the right side 154 and the rear side 152 of the insulating block 130, respectively. Further, FIG. 8 is a sectional view of the forceps jaw assembly 109 taken along the line VIII—VIII in FIG. 4.

The right side 154 of the insulating block 130 is provided with a first protrusion 154a. The first protrusion 154a has a substantially flat side surface 154b. Similarly, the left side 156 of the insulating block 130 is provided with a second protrusion 156a which also has a substantially flat side surface 156b. The first and second protrusions 154a and 154b are formed such that the distance between the side surfaces 154b and 156b of the first and second protrusions 154a and 156a, or the total width of the insulating block 130, is substantially same as the width of the slit 124. Thus, the side surfaces 154b and 156b of the first and second protrusions 154a and 156a come in contact with the right and left inner side surface 124a and 124b of the slit 124 when the insulating block 130 is located in the slit 124.

Figure 8:
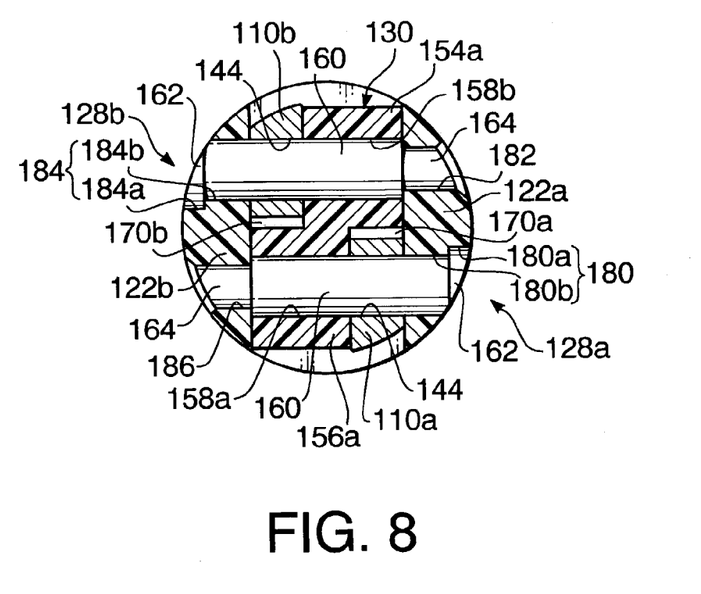
FIG. 8 is a sectional view of the forceps jaw assembly taken along the line VIII—VIII in FIG. 4.

As shown in FIG. 8, first and second protrusions 154a and 154b serve to form first and second spaces 170a and 170b between the insulating block 130 and the arms 122 of the clevis 120 for receiving the first and second jaws 110a and 110b, respectively.

The first and second jaws 110a and 110b are pivotably coupled to the first and second rivets 128a and 128b within the first and second spaces 170a and 170b, respectively.

The first and second protrusions 154a and 156a are formed such that the widths of the first and second spaces 170a and 170b become slightly larger than the widths of the first and second jaws 110a and 110b, respectively. Thus, the first and second jaw 110a and 110b can smoothly swing about the first and second rivets 128a and 128b, respectively.

As can be seen in FIG. 8, the first protrusion 154a is formed such that it surrounds the second rivet 128b in the vicinity of the first jaw 110a and the second protrusion 156a is formed such that it surrounds the first rivet 128a in the vicinity of the second jaw 110b. The first and second protrusions configured as above prevent the first and second jaws 110a and 110b from coming into contact with the second and first rivets 128a and 128b, respectively, and making a short circuit.

As shown in FIG. 8, the first arm 122a of the clevis 120 is provided with two bores 180 and 182, and the second arm 122b is also provided with two bores 184 and 186.

Each of the bores 180 and 184 includes a large diameter portion (180a, 184a) and a small diameter portion (180b, 184b), which have substantially the same diameters as the head 162 and body 160 of the rivets (128a, 128b), respectively. The other two bores 182 and 186 are formed in substantially the same diameter as the tip portions of the rivets (128a, 128b).

The first rivet 128a is coupled to the clevis 120 by inserting it into the bores 180 and 186 in a direction from right to left in FIG. 8. Similarly, the second rivet 128b is coupled to the clevis 120 by inserting it into the bores 182 and 184 in the opposite direction of the first rivet 128a, i.e. from left to right in FIG. 8. The head 162 of the first rivet 128a (the second rivet 128b) inserted into the bore 180 (184) fits into the large diameter portion 180a (184a) of the bore 180 (184). A stepped portion formed between the large diameter portion 180a (184a) and the small diameter portion 180b (184b) prevents the head 162 of the first rivet 128a (the second rivet 128b) from passing through the bore 180 (184). The end portions of the rivets 128a and 128b are swaged so that the rivets 128a and 128b do not come off from the clevis 120.

As described above, the first and second rivets 128a and 128b are coupled to the clevis 120 in opposite directions. Thus, the swaged portions of the rivets (128a, 128b), which have lower mechanical strength than the heads 162 thereof, are located at different arms (122a, 122b) of the clevis 120.

If an external force is exerted on the arms (122a, 122b) of the clevis 120 that acts to widen the width of the slit 124, the head 162 of the first rivet 128a prevents the first arm 122a from bending outwardly and coming disengaged with the tip portion 164 of the second rivet 128b. Similarly, the head 162 of the second rivet 128b prevents the tip portion 164 of the first rivet 128a from coming off from the second arm 122b of the clevis 120. Thus, the forceps assembly 109 does not disassemble due to an external force.

Figure 9:
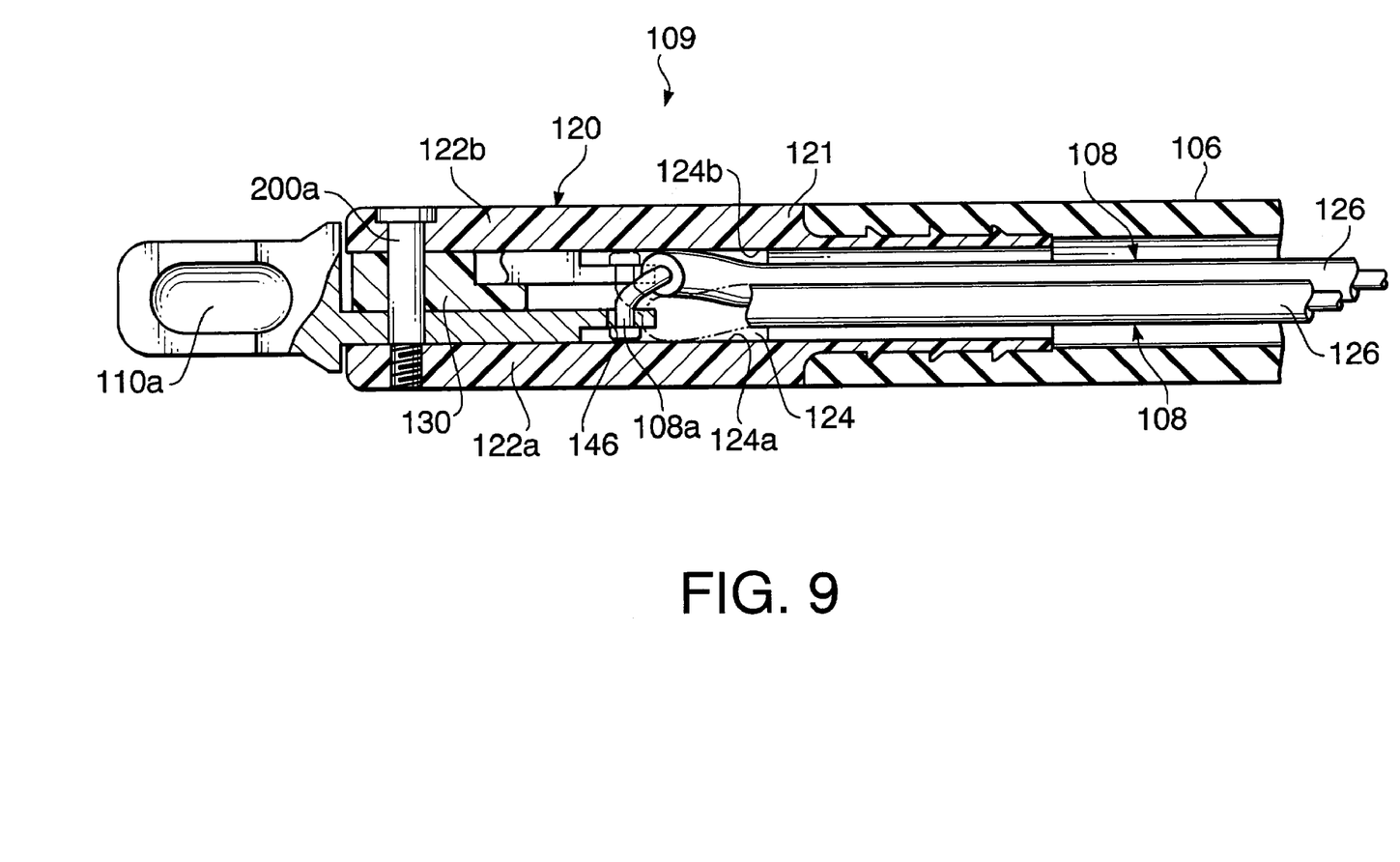
FIG. 9 is a sectional view of an end portion of a variation of the endoscopic forceps instrument shown in FIGS. 2 through 8.

FIG. 9 is a sectional view of an end portion of a variation of the endoscopic forceps instrument 100 shown in FIGS. 2 through 8. In the endoscopic forceps instrument shown in FIG. 9, first and second rivets 128a and 128b are replaced with first and second pins 200a and 200b (only first pins 200a is shown in FIG. 9), which are made from metal such as stainless steel, for example. The tip portion of the first and second pins 200a and 200b are provided with a thread and screw coupled with the corresponding bore (182, 184). Except the above, the variation of the endoscopic forceps instrument shown in FIG. 9 has essentially the same configuration as the endoscopic forceps instrument shown in FIGS. 2 through 8.

Figure 10:
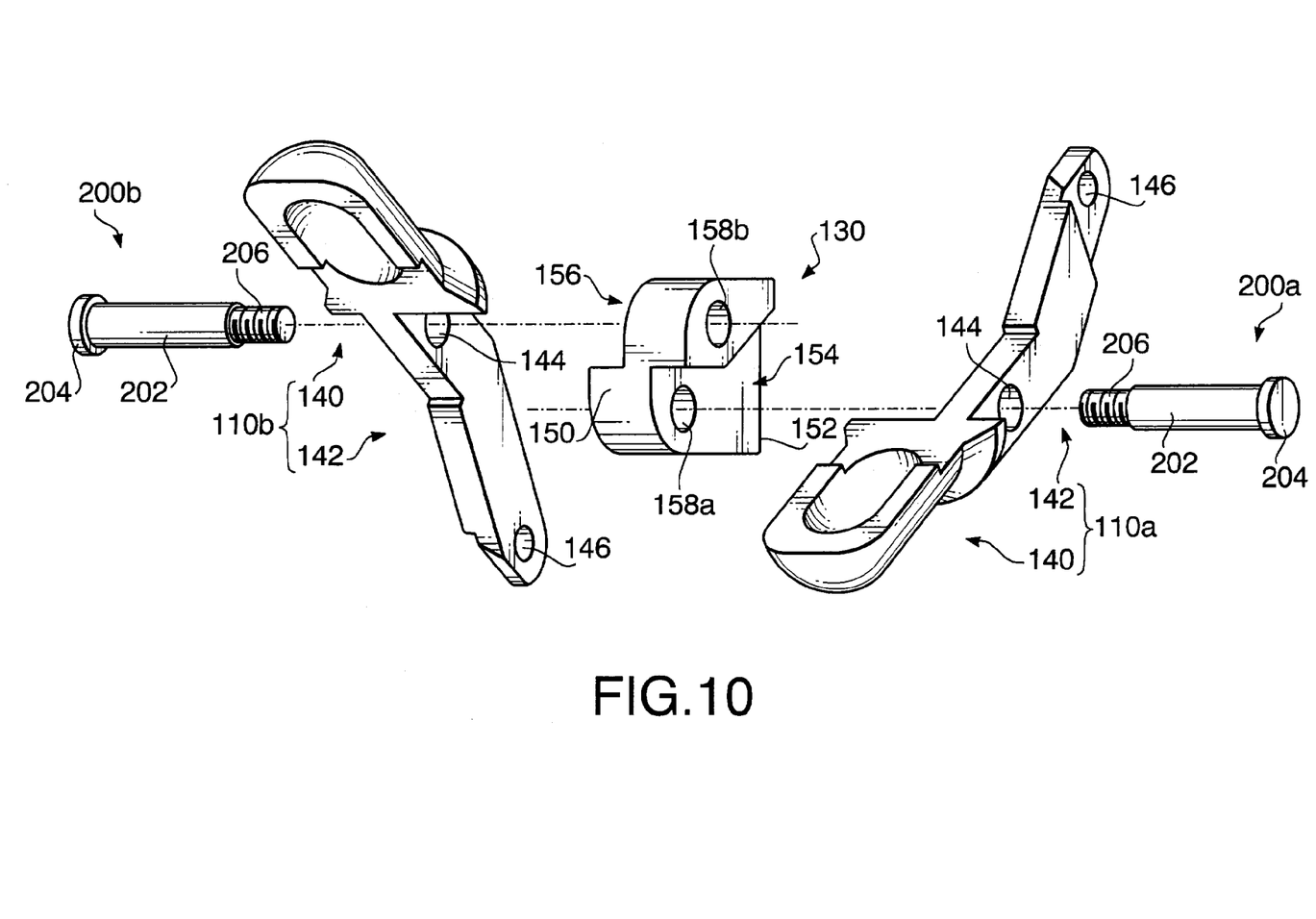
FIG. 10 is an exploded perspective view of the forceps jaw assembly of the variation of the endoscopic forceps instrument shown in FIG. 9.

FIG. 10 is an exploded perspective view of the forceps jaw assembly of the endoscopic forceps instrument shown in FIG. 9, in which the first and second pins 200a and 200b are used instead of the first and second rivets 128a and 128b. Note that the clevis 120 is not shown in FIG. 10 for clarity of the drawing.

As shown in FIG. 10, each of the first and second pins 200a and 200b has a body 202, a head 204 having a larger diameter than the body 202, and a tip portion 206 having a smaller diameter than the body 202. As mentioned above, a thread is formed to each of the tip portions 206. The first and second pins are arranged such that the tip portions 206 thereof are coupled to opposite arms (122a, 122b) of the clevis 120, or the heads 204 are coupled at different arms (122a, 122b). Thus, the heads 204 of the pins (200a, 200b) prevents the tip portions 206 thereof from disengaging from the arms (122a, 122b) as like in the endoscopic forceps instrument shown in FIGS. 1 through 8.

The insertion portion 104 of forceps instrument 100 configured as above is introduced into a body cavity such as a stomach through an endoscope and the forceps jaw assembly 109 are located in the vicinity of a target portion such as a bleeding portion.

Then, the operation portion 102 is operated such that the pair of conductive wires 108 is slid forwards within the sheath 106 and swing the first and second jaws 110a and 110b to the open position. Then, the jaws 110a and 110b are moved by the endoscope such that bleeding portion is located between the jaws 110a and 110b.

Next, the pair of conductive wires 108 are retracted by pulling back the rod portion 114 with respect to the cylindrical portion 112 to move the front portions 140 of the jaws 110a and 110b to the closed position and thereby grasping the bleeding portion.

Next, a high frequency electrical power is supplied from the power supply 200 to the first and second jaws 110a and 110b via the conductive wires 108. As a result, a high frequency current flows through the bleeding portion placed between the jaws 110 to coagulate the bleeding portion and thereby stop bleeding therefrom.

The invention has been described in detail with particular reference to an embodiment thereof, but it will be understood that variations and modifications can be effected within the spirit and scope of the invention. For example, although the forceps instrument described above is supplied with high frequency electric power, the invention can be applied also to forceps instruments that do not utilize high frequency electric power.

The present disclosure relates to the subject matters contained in Japanese Patent Applications No. P2002-106012, filed on Apr. 9, 2002, and No. P2002-278651, filed on Sep. 25, 2002, which are expressly incorporated herein by reference in their entireties.

What is claimed is:

1. An endoscopic forceps instrument having an inserting portion to be inserted into a body cavity through an endoscope, comprising:
   a clevis coupled to a distal end of said inserting portion;
   a pair of rivet members that extend through bores formed in said clevis to be coupled to said clevis, each of said rivet members having a head at one end thereof and an engaging portion at other end thereof, said head having a shape and size that does not allow said head to pass through said bores, said engaging portion being engaged with said clevis to fix said rivet member to said clevis, said rivet members being arranged parallel to each other and such that said heads are located at opposite sides of said clevis; and
   a pair of opposing jaws pivotably coupled to respective rivet members so as to be movable between an open position and a closed position.

2. The endoscopic forceps instrument according to claim 1, wherein said engaging portion is a tip end of said rivet member, said tip end being swaged to fix said rivet member to said clevis.

3. The endoscopic forceps instrument according to claim 1, wherein said engaging portion is screw coupled with said clevis.

4. The endoscopic forceps instrument according to claim 1, wherein said rivet members are arranged such that a longitudinal axis of said clevis passes through a space defined between said rivet members.

5. The endoscopic forceps instrument according to claim 1, wherein said pair of jaws comprise a conductive material and are connected to a pair of wires for being supplied with high frequency electric power.

6. The endoscopic forceps instrument according to claim 5, further comprising, an insulating block supported by said rivet members between said pair of jaws.

7. A forceps jaw assembly, comprising:
   a clevis having a base couplable to a distal end of an inserting portion of an endoscopic forceps instrument;
   a pair of rivet members that extend through bores in said clevis to be coupled to said clevis, each of said rivet members having a head at one end thereof and an engaging portion at other end thereof, said head having a shape and size that does not allow said head to pass through said bores, said engaging portion being engaged with said clevis to fix said rivet member to said clevis, said rivet members being arranged parallel to each other and such that said heads are located at opposite sides of said clevis; and
   a pair of opposing jaws pivotably coupled to respective rivet members so as to be movable between an open position and a closed position.

8. The endoscopic forceps instrument according to claim 7, wherein said engaging portion is a tip end of said rivet member, said tip end being swaged to fix said rivet member to said clevis.

9. The endoscopic forceps instrument according to claim 7, wherein said engaging portion is screw coupled with said clevis.

10. The forceps jaw assembly according to claim 7, wherein said rivet members are arranged such that a longitudinal axis of said clevis passes through a space defined between said rivet members.

11. The forceps jaw assembly according to claim 7, wherein said pair of jaws comprise a conductive material and are connected to a pair of wires for being supplied with high frequency electric power.

12. The forceps jaw assembly according to claim 11, further comprising, an insulating block supported by said rivet members between said pair of jaws.

* * * * *